United States Patent

Butcher et al.

[11] Patent Number: 5,631,251
[45] Date of Patent: May 20, 1997

[54] 5-CYCLOPROPYL-1,4 BENZODIAZEPINE-2-ONES

[75] Inventors: John Butcher, Telford; David A. Claremon, Maple Glen; Nigel Liverton, Harleysville; Harold G. Selnick, Ambler, all of Pa.

[73] Assignee: Merck & Co., Inc., Rahway, N.J.

[21] Appl. No.: 481,662

[22] Filed: Jun. 7, 1995

[51] Int. Cl.$^6$ .................. A61K 31/55; C07D 243/24
[52] U.S. Cl. ............................ 514/221; 540/509
[58] Field of Search ..................... 540/504, 509; 514/221

[56] References Cited

U.S. PATENT DOCUMENTS

| | | | |
|---|---|---|---|
| 4,470,988 | 9/1984 | Watthey | 424/263 |
| 4,473,575 | 9/1984 | Watthey | 424/263 |
| 4,503,060 | 3/1985 | Walther et al. | 514/214 |
| 4,507,313 | 3/1985 | Braestrap et al. | 514/220 |
| 4,537,885 | 8/1985 | Watthey | 514/183 |
| 4,600,534 | 7/1986 | Bach et al. | 260/234.3 |
| 4,692,522 | 9/1987 | Parsons et al. | 540/523 |
| 4,775,671 | 10/1988 | Hunkeler et al. | 514/220 |
| 4,820,834 | 4/1989 | Evans et al. | 540/504 |
| 4,847,248 | 7/1989 | Freidinger et al. | 514/214 |
| 4,992,437 | 2/1991 | Naka et al. | 514/220 |
| 5,004,741 | 4/1991 | Evans et al. | 514/221 |
| 5,055,464 | 10/1991 | Murakami et al. | 514/211 |
| 5,166,151 | 11/1992 | Freidinger et al. | 514/215 |
| 5,206,234 | 4/1993 | Bock et al. | 514/213 |
| 5,220,018 | 6/1993 | Bock et al. | 540/509 |
| 5,302,591 | 4/1994 | Fletcher et al. | 514/221 |
| 5,324,726 | 6/1994 | Bock et al. | 514/221 |
| 5,338,861 | 8/1994 | Botta et al. | 548/552 |
| 5,360,802 | 11/1994 | Chambers et al. | 514/221 |
| 5,410,049 | 4/1995 | Chambers | 540/504 |
| 5,426,185 | 6/1995 | Baldwin et al. | 540/509 |
| 5,438,055 | 8/1995 | Baldwin et al. | 540/509 |
| 5,439,905 | 8/1995 | Naka et al. | 514/220 |
| 5,439,906 | 8/1995 | Bock et al. | 514/220 |
| 5,504,077 | 4/1996 | Collins et al. | 514/211 |

FOREIGN PATENT DOCUMENTS

| | | |
|---|---|---|
| 1190708 | 7/1985 | Canada . |
| 0107095A1 | 5/1984 | European Pat. Off. . |
| 0514133A1 | 11/1992 | European Pat. Off. . |
| 0538945A1 | 4/1993 | European Pat. Off. . |
| 0566175A2 | 10/1993 | European Pat. Off. . |
| WO93/02078 | 2/1993 | WIPO . |
| WO93/08176 | 4/1993 | WIPO . |
| WO93/07131 | 4/1993 | WIPO . |
| WO93/15068 | 8/1993 | WIPO . |
| WO93/19063 | 9/1993 | WIPO . |
| WO93/17011 | 9/1993 | WIPO . |
| WO94/05673 | 3/1994 | WIPO . |

OTHER PUBLICATIONS

J. Gen. Physiol., vol. 96, pp. 195–215 (Jul. 1990), by M. C. Sanguinetti, et al.

J. Cardiovasc. Pharmacol., vol. 20, (Suppl. 2) pp. S17–S22 (1992), by L. M. Hondeghem.

*Primary Examiner*—Joseph McKane
*Assistant Examiner*—Richard S. Myers, Jr.
*Attorney, Agent, or Firm*—Elliott Korsen; Francis P. Bigley; Mark R. Daniel

[57] ABSTRACT

This invention is concerned with novel compounds represented by structural formula I

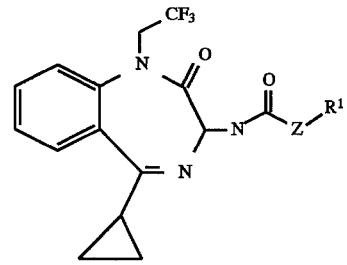

FORMULA I

Z is $C_{0-6}$ alkyl; and $R^1$ is phenyl or mono or disubstituted phenyl, where the substitutents are Cl, and $CF_3$, or pharmaceutically acceptable salts, hydrates and crystal forms thereof which are useful in the treatment of arrhythmia.

13 Claims, No Drawings

5-CYCLOPROPYL-1,4 BENZODIAZEPINE-2-ONES

BACKGROUND OF THE INVENTION

Arrhythmias often occur as complications to cardiac diseases such as myocardial infarction and heart failure. In a serious case, arrhythmias give rise to a ventricular fibrillation and can cause sudden death.

Though various antiarrhythmic agents are now available on the market, agents which exhibit both satisfactory effects and high safety profiles have not been marketed. For example, antiarrhythmic agents of Class I, according to the classification of Vaughan-Williams, which cause a selective inhibition of the maximum velocity of the upstroke of the action potential (Vmax) are inadequate for preventing ventricular fibrillation. In addition, they have problems regarding safety, namely, they cause a depression of the myocardial contractility and have a tendency to induce arrhythmias due to an inhibition of the impulse conduction. Beta-adrenoceptor blockers and calcium antagonists which belong to Class II and IV respectively, have a defect in that their effects are either limited to a certain type of arrhythmia or are contraindicated because of their cardiac depressant properties in certain patients with cardiovascular disease. Their safety, however, is higher than that of the antiarrhythmic agents of Class I.

Antiarrhythmic agents of Class III are drugs which cause a selective prolongation of the duration of the action potential without a significant depression of the Vmax. Drugs in this class are limited. Examples such as sotalol and amiodarone have been shown to possess Class III properties. Sotalol also possesses Class II effects which may cause cardiac depression and be contraindicated in certain susceptible patients. Also, amiodarone is severely limited by side effects. Drugs of this class are expected to be effective in preventing ventricular fibrillations Pure Class III agents, by definition, are not considered to cause myocardial depression or an induction of arrhythmias due to the inhibition of the action potential conduction as seen with Class I antiarrhythmic agents.

SUMMARY OF THE INVENTION

This invention is concerned with novel compounds represented by structural formula I

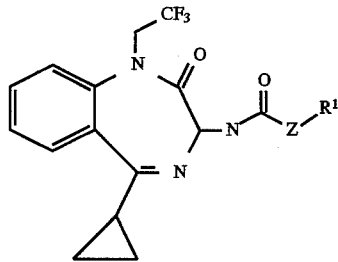

FORMULA I where

Z is $C_{0-6}$ alkyl; and $R^1$ is phenyl or mono or disubstituted phenyl, where the substitutents are Cl, and $CF_3$, or pharmaceutically acceptable salts, hydrates and crystal forms thereof, which are useful as antiarrhythmic agents.

The compounds of the present invention may have asymmetric centers and occur as racemates, mixtures of enantiomers, individual diastereomers, or as individual enantiomers with all isomeric forms being included in the present invention. The invention is also concerned with pharmaceutical formulations comprising one of the novel compounds as an active ingredient.

The invention is also concerned with a method of treating arrhythmia by the administration of one or a combination of the novel compounds or formulation thereof to a patient in need of such treatment.

DETAILED DESCRIPTION OF THE INVENTION

The novel compounds of this invention have structural formulae

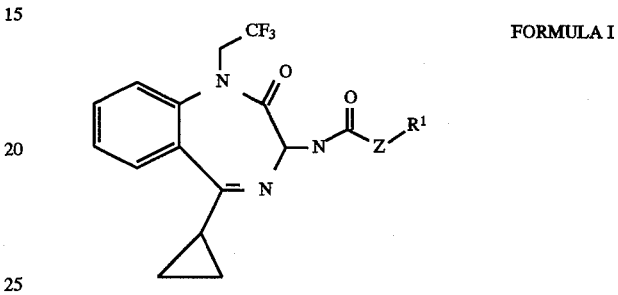

FORMULA I where

Z is $C_{0-6}$ alkyl; and $R^1$ is phenyl or mono or disubstituted phenyl, where the substitutents are Cl, and $CF_3$, or pharmaceutically acceptable salts, hydrates and crystal forms thereof, which are useful as antiarrhythmic agents.

The compounds of the present invention may have asymmetric centers and occur as racemates, mixtures of enantiomers, individual diastereomers, or as individual enantiomers with all isomeric forms being included in the present invention. The invention is also concerned with pharmaceutical formulations comprising one of the novel compounds as an active ingredient.

The invention is also concerned with a method of treating arrhythmia by the administration of one or a combination of the novel compounds or formulation thereof to a patient in need of such treatment These compounds include pharmaceutically acceptable crystal forms and hydrates of the compounds of Formula I, which are antiarrhythmic agents.

One embodiment of the novel compounds of this invention is (+)-2-(2,4-Dichloro-phenyl)-N-[2,3-dihydro-1-(2,2,2-trifluoroethyl)-2-oxo-5-cyclopropyl-1H-1,4-benzodiazepin-3-yl]acetamide.

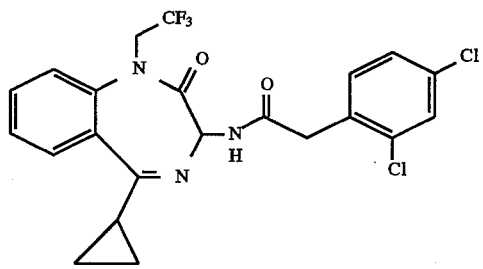

An other embodiment of this invention is (+)-2-(3,4-Dichlorophenyl)-N-[2-oxo-5-cyclopropyl-1-(2,2,2-trifluoroethyl)-2,3-dihydro-1H-benzo[e][1,4]diazepin-3-yl]-acetamide.

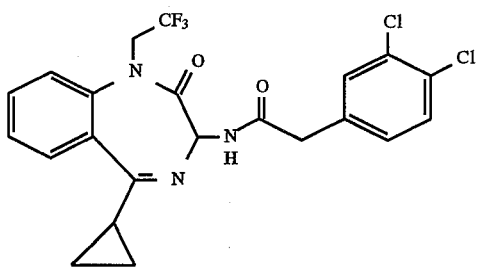
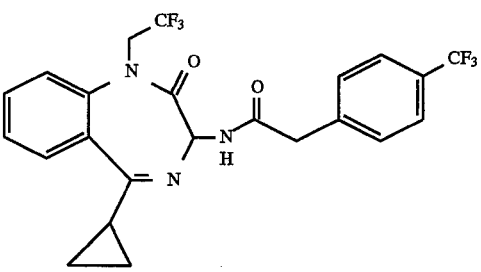

Still an other embodiment of this invention is (+)-2-(3,5-Dichlorophenyl)-N-[2-oxo-5-cyclopropyl-1-(2,2,2-trifluoroethyl)-2,3-dihydro-1H-benzo[e][1,4]diazepin-3-yl] acetamide A further embodiment of this invention is (+)-2-(3,5-Bis-trifluoromethylphenyl)-N-[2-oxo-5-cyclopropyl-1-(2,2,2-trifluoroethyl)-2,3-dihydro-1H-benzo[e][1,4]diazepin-3-yl]-acetamide.

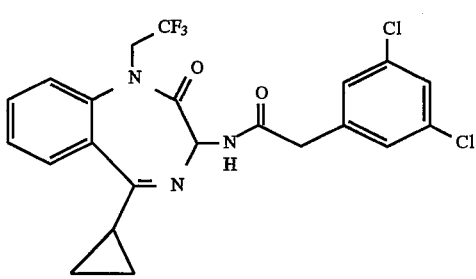
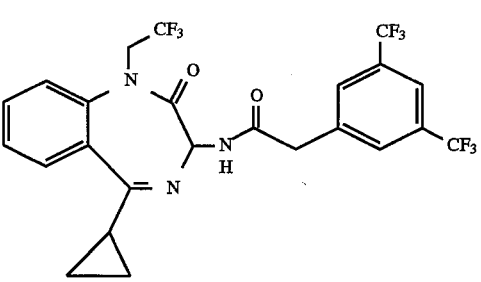

An other embodiment of this invention is (+)-3-(2,4-Dichlorophenyl)-N-[2-oxo-5-cyclopropyl-1-(2,2,2-trifluoroethyl)-2,3-dihydro-1H-benzo[e][1,4]diazepin-3-yl] propanamide Yet an other embodiment of this invention is (+)-2-(2,4-Bis-trifluoromethylphenyl)-N-[2-oxo-5-cyclopropyl-1-(2,2,2-trifluoroethyl)-2,3-dihydro-1H-benzo[e][1,4]diazepin-3-yl]acetamide.

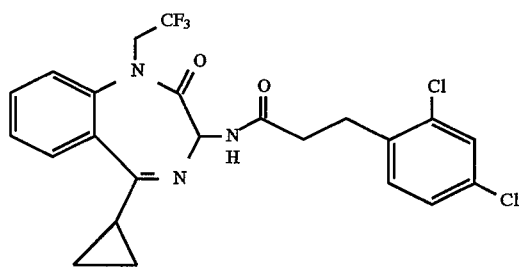
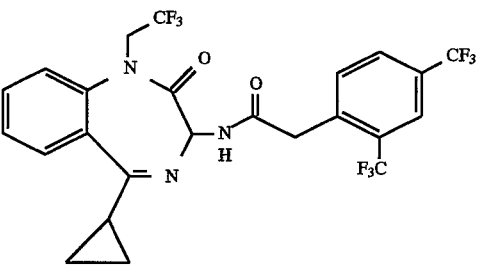

An additional embodiment of this invention is (+)-2-(4-Trifluoromethylphenyl)-N-[2-oxo-5-cyclopropyl-1-(2,2,2-trifluoroethyl)-2,3-dihydro-1H-benzo[e][1,4]diazepin-3-yl] acetamide.

The compounds of this invention may be synthesized using the procedures explained in the Examples below and using the following scheme.

Scheme 1

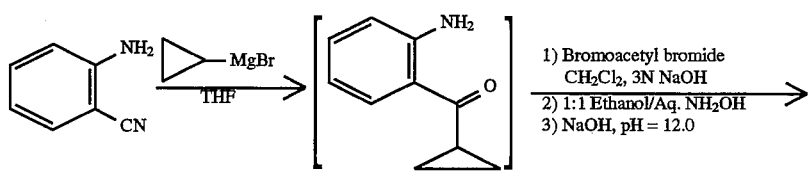

5
-continued
Scheme 1
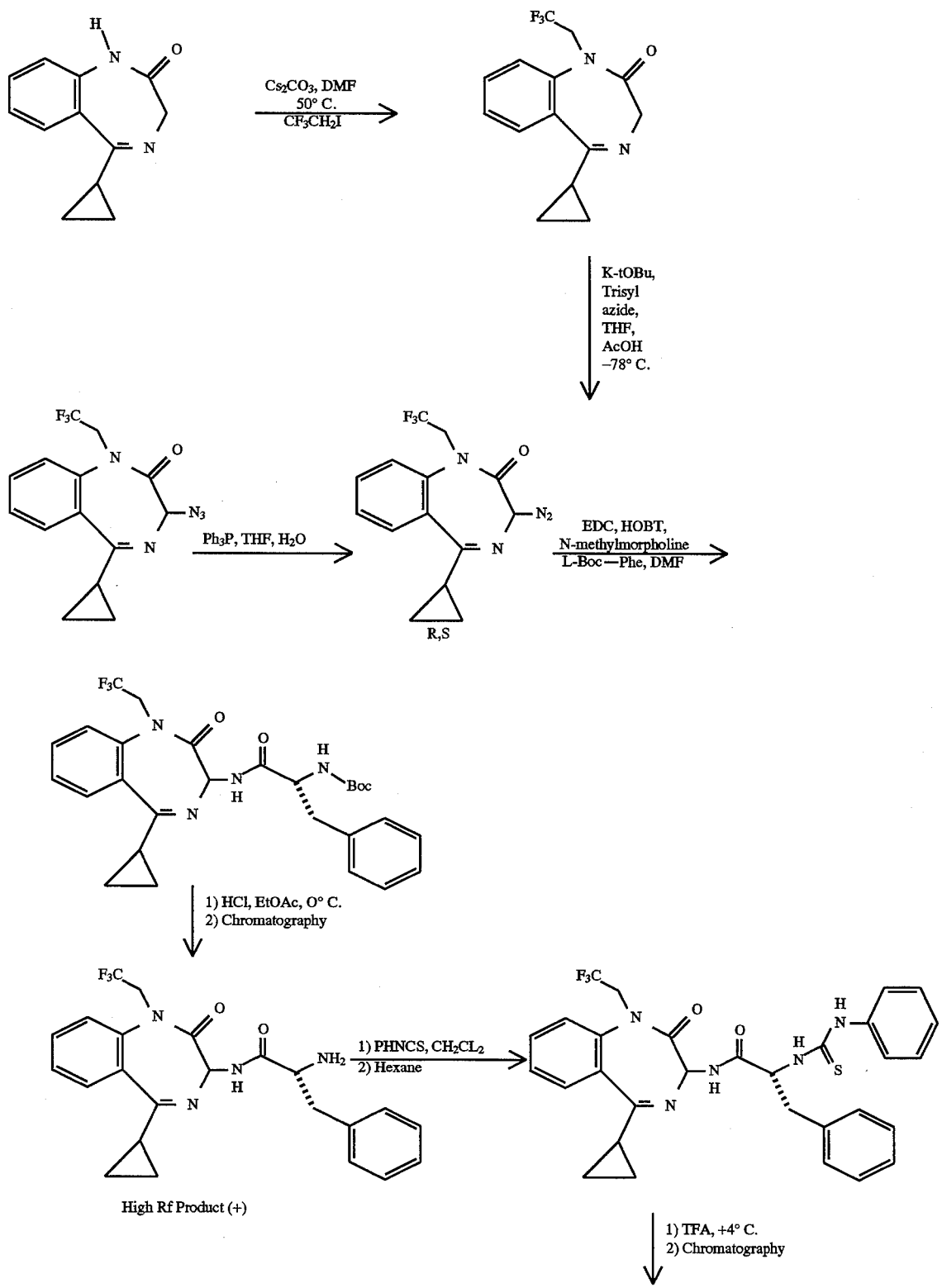

-continued
Scheme 1

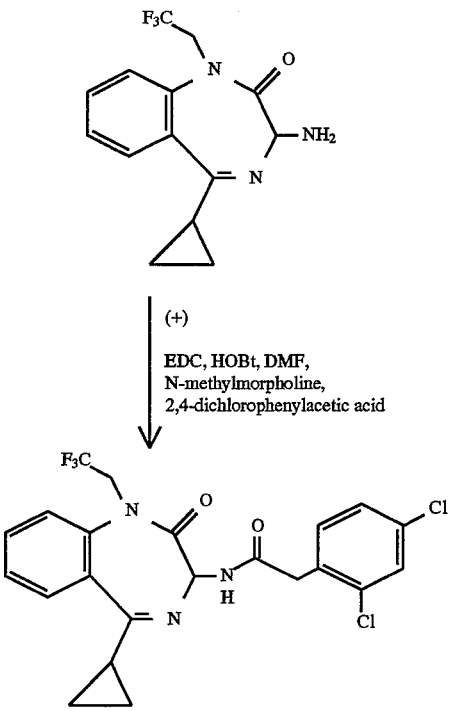

The novel compounds of the instant invention have the pharmacological properties required for antiarrhythmic agents of Class III, namely the prolongation of the myocardial action potential in vitro, without a significant depression of the Vmax, and the prolongation of QTc-interval in anesthetized dogs.

These compounds are effective in treating and preventing all types of arrhythmias including ventricular and atrial (supra-ventricular) arrhythmias. The compounds of the present invention are especially useful to control reentrant arrhythmias and prevent sudden death due to the ventricular fibrillation. These compounds are also effective in treating and preventing impaired cardiac pump functions.

In the novel method of this invention of treating arrhythmia, one of the compounds or pharmaceutically acceptable salt thereof, is administered in an amount ranging from about 0.0001 to about 20 mg per kg of body weight per day, preferably from about 0.001 to about 5.0 mg per kg of body weight per day in a single dose or in 2 to 4 divided doses.

These compounds, or pharmaceutically acceptable salts thereof, in the described dosages, are administered orally, intraperitoneally, subcutaneously, intramuscularly, transdermally, sublingually or intravenously. They are preferably administered intravenously or orally, for example in the form of tablets, troches, capsules, elixirs, suspensions, emulsions, syrups, wafers, chewing gum, or the like prepared by art recognized procedures. The amount of active compound in such therapeutically useful compositions or preparations is such that a suitable dosage will be obtained.

These compounds can be administered as the sole active ingredient or in combination with other antiarrhythmic agents or other cardiovascular agents, such as Class I, Class II or Class IV antiarrhythmic agents, vasodilators, angiotensin converting enzyme inhibitors, angiotensin II antagonists, diuretics or digitalis.

These compounds can be administered as a method of treating arrhythmia and impaired cardiac pump functions in conjunction with defibrillators, including implantable defibrillators. These compounds reduce the frequency of defibrillator firing.

By Class I antiarrhythmic agents is meant those agents which provide for sodium channel blockade, including those compounds which exert a membrane stabilizing effect. Exemplary of this class of compounds are quinidine, procainamide, disopyramide, lidocane, tocainide, flecainide and propafenone. By Class II antiarrhythmic compounds is meant those agents which block sympathetic activity. Exemplary of this class of compounds are propranolol and acebutolol. By Class III antiarrhythmic agents is meant those compounds which prolong the effective refractory period without altering the resting membrane potential or rate of depolarization. In addition to the novel compounds of this invention; compounds such as amiodarone, bretylium and sotalol are considered to be in this class. Class IV antiarrhythmic agents are effective in calcium channel blockade. Exemplary of this class of compounds are diltiazem and verapamil. Further definition of these classes can be found in Pharma Projects, section C1B, May 1993, which is hereby incorporated by reference.

Exemplary of vasodilators are compounds such as papaverine and isosorbide dinitrat. Examples of angiotensin converting enzyme inhibitors include enalapril, lisinopril and captopril. Examples of diuretics include hydrochlorothiazide and acetazolamide. The pharmaceutical agents listed herein are examples and do not represent a complete listing of the many compounds in these classes which are contemplated by this invention.

The activity of the compounds described herein as antiarrhythmic agents is measured by their ability to block the IKs and IKr currents as determined by the following test protocol.

Outward potassium currents are measured in single guinea pig ventricular myocytes using a whole-cell voltage clamp technique described in detail elsewhere (Sanguinetti and Jurkiewicz, 1990, Two components of cardiac delayed rectifier K+ current: differential sensitivity to block by Class III antiarrhythmic agents. J. Gen Physiol. 96: 195–215). Myocytes are isolated by enzymatic (collagenase and protease) digestion of Langandorf perfused hearts. Single cells are then voltage clamped using 1 mm square-bore pipettes filled with 0.5M Kgluconate, 25 mM KCl, 5 mM K(2)ATP. Cells are bathed in a solution containing, in mN: 132 NaCl, 4KCl, 1.2 MgCl[2], 10 HEPES, 10, glucose: pH 7.2, temp. 35° C.

Each cell is maintained at a holding potential of −50 mV. Test depolarizations are applied as voltage ramps from −85 to −50 mV, and as steps to −10 mV (0.5 s) and +50 mV (1.0 s). IKl is measured as peak outward current during the voltage ramp. IKr is measured as tail currents upon repolarization from −10 mV to −50 mV. IKs is measured as time-dependent current during the pulse to +50 mV. Currents are measured during control, then after exposure to drug at two different concentrations.

Employing this test the compounds described herein have an $IC_{50}$ of less than 1,000 nM as IKs blockers. The compounds of this invention are at least 10 times more potent in the blockade of IKs than the blockade of IKr.

EXAMPLES

Example 1

(+)-2-(2,4-Dichlorophenyl)-N-[2,3-dihydro-1-(2,2,2-trifluoroethyl)-2-oxo-5-cyclopropyl-1H-1,4-benzodiazepin-3-yl]acetamide.

Scheme 1

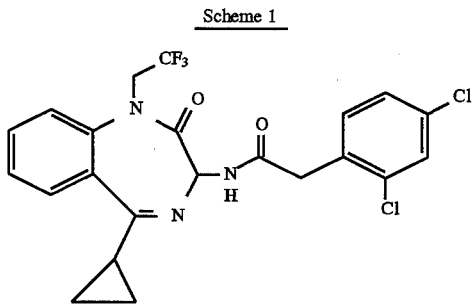

Step A.: 5-cyclopropyl-1,4-benzodiazepine-2-one

To a solution of anthranilonitrile (85 g, 0.720 mole) in THF (1.0 L) at −10° C. was slowly added a 1.6 M solution of cyclopropyl magnesium bromide in THF (1.55 L, 2.48 mole). The reaction was allowed to stir overnite at room temperature then slowly quenched into a −10° C. solution of 4N HCL (1.2 L). The mixture was stirred for 1 hour at room temperature and the pH adjusted to 7.5 with 10N sodium hydroxide. The THF layer was removed, the aqueous layer washed with ethyl acetate (800 mL), and the organic extracts concentrated in vacuo to a dark oil. The oil was dissolved in methylene chloride (1.2 L), washed with water (500 mL), dried over sodium sulfate, and filtered. To the methylene chloride filtrate at 0° C. was slowly added bromoacetyl bromide (168.0 g, 0.836 mole) followed by 3N sodium hydroxide (800mL). The reaction was allowed to stir for 1 hour and the pH of the mixture adjusted to 7.5 with concentrated hydrochloric acid. The methylene chloride layer was removed and the aqueous layer washed with methylene chloride (1.0 L). The methylene chloride extracts were washed with 5% aqueous sodium bicarbonate, dried over sodium sulfate, filtered and concentrated to an oil. The oil was dissolved in ethanol (1.5 L) added to a 50% solution of ethanol/aqueous ammonium hydroxide (6.3 L) and allowed to stir for 48 hours. The reaction mixture was concentrated in vacuo to 2.7 L and the pH adjusted to 12.0 with 50% sodium hydroxide. After stirring at pH=12 for 1 hour the reaction pH was adjusted to 8.5 with concentrated hydrochloric acid and solids filtered. The cake was washed with water (1.0 L), sucked dry and dried in vacuo at 40° C. to give 102.2 g, (71%). ¹H NMR (CDCl₃, 300 MHz) δ9.45 (s, 1H) 7.84 (dd, J=8.0 and 1.6 Hz,1H), 7.45 (dt, J=8.0 and 1.6 Hz, 1H), 7.24 (dt, J=8.0 and 1.6 Hz,1H), 7.12 (dd, J=8.0 and 1.6 Hz, 1H),4.04 (br s. 2H), 1.95 (m,1H), 0.9–1.2 (m, 4H)

Step B. Preparation of 2,3-dihydro-1-(2,2,2-trifluoroethyl)-2-oxo-5-cyclopropyl-1H-1,4-benzodiazepine.

A solution of 5-cyclopropyl-1,4-benzodiazepine-2-one (50 g, 0.250 mole) in DMF (250 mL) was treated with cesium carbonate (244 g, 0.750 mole) and trifluoroethyl iodide.(157.5 g, 0.750 mole). The mixture was stirred at 50° C. overnight. The reaction was cooled to room temperature and filtered. The solids were washed with ethyl acetate and the filtrates concentrated in vacuo, diluted to an oil. The residue was chromatographed on silica using 20% ethyl acetate/hexane to give upon concentration of product cuts 46.2 g (65.5%) oil which solidified on standing.

¹H NMR (CDCl₃, 300 MHz) δ7.78 (dd, J=9.2 and 1.6 Hz, 1H), 7.53 (dt, J=9.2 and 1.6 Hz, 1H), 7.35 (dt, J=8.3 and 1.3 Hz,1H), 7.29 (br d, J=8.3 Hz, 1H), 5.10 (dq, J=15, 9,2 Hz, 1H), 4.52 (d, J =11.1 Hz, 1H), 4.12 (sextet, J=9.2 Hz, 1H), 3.62 (d,J=11.1 Hz, 1H), 2.02 (m, 1H), 0.9–1.2 (m, 4H)

Step C.: Preparation of 3-Azido-5-cyclopropyl-1-(2,2,2-trifluoroethyl)-1H-benzo[e][1,4]diazepine.

To a stirring solution of 5-cyclopropyl-1-(2,2,2-trifluoroethyl)-1H-benzo[e][1,4]diazepine (21 g, 0.0744 mol) in THF (525 ml) cooled to −78° C. was added potassium tert-butoxide (2.05 eq, 0.153 mol, 153 ml of a 1M solution in THF) dropwise over 15 min. A solution of 2,4,6-Triisopropylphenylsulfonylazide (25.3 g, 0.082 mol) in THF (300 ml) was added over 5 min. This was stirred for 10 min, acetic acid (18.6 ml,0.325 mol) was added and the reaction warmed to 30° C. for 1 hour. The reaction was concentrated the residue dissolved in ethyl acetate (1 L) and washed with satd. NaHCO₃ (500 ml). The aqueous layer was back extracted with ethyl acetate(200ml). The organic layers were combined, dried with Na₂SO₄ and evaporated to a brown foam. This was chromatographed over silica eluting with 20% ethyl acetate:hexane. The appropriate fractions were collected and evaporated under reduced pressure to give 20.1 g (84%) of a white powder.

¹H NMR (CDCl₃, 300 MHz) δ7.81 (dd, J=8.0 and 1.6 Hz,1H), 7.58 (dt, J=8.0 and 1.6 Hz,1H), 7.38 (dt, J=8.0 and 1.3 Hz,1H), 7.33 (br d, J=8.0 Hz,1H), 5.18 (dq, J=24 and 9.1 Hz,1H), 4.42 (s,1H), 4.35 (approx. sextet, J=9.1 Hz,1H), 2.02 (m,1H), 0.9–1.4 (m, 4H).

Step C.: Preparation of 3-Amino-5-cyclopropyl-1-(2,2,2-trifluoroethyl)-1H-benzo[e][1,4]diazepine.

To a stirred solution of 3-Azido-5-cyclopropyl-1-(2,2,2-trifluoroethyl)-1H-benzo[e][1,4]diazepine (18.0 g, 55.7 mmol) in THF (180 mL) was added triphenylphosphine (44.0 g, 0.167 mol) and water (10.0 ml, 0.56 mol). This was stirred overnight at ambient temperature The reaction was then concentrated under reduced pressure, taken up in 1N HCl (300 mL), and extracted with ethyl ether (3×100 ml). The combined organics were back extracted with 1N HCl (100 ml). The combined aqueous layers were basified with 50% NaOH until pH=10. This was extracted with ethyl acetate (2×500 mL). The combined ethyl acetate fractions were dried over Na₂SO₄, evaporated under reduced pressure to give 15.7 g of a tan solid.

¹H NMR (CDCl₃, 300 MHz) δ7.78 (dd, J=8.0 and 1.7 Hz,1H), 7.54 (dt, J=8.0 and 1.7 Hz,1H), 7.36 (dt, J=8.0 and 1.7 Hz, 1H), 7.30 (br d, J=8.0 Hz,1H), 5.10 (dq, J=25 and 9 Hz,1H), 4.35 (s,1H), 4.15 (approx. sextet, J=8.0 Hz, 1H), 2.22 (br s, 2H), 1.98 (m, 1H), 0.9–1.15 (m, 4H).

Step C. Preparation of 2-(tert-Butoxycarbonylamino)-N-[2-oxo-5-cyclopropyl-1-(2,2,2-trifluoroethyl)-2,3-dihydro-1H-benzo[e][1,4]diazepin-3-yl]-3-phenyl-propionamide.

To a mixture of 3-amino-5-cyclopropyl-1-(2,2,2-trifluoroethyl)-1H-benzo[e][1,4]diazepine (15.0 g, 50.5 mmol), Boc-L-phenylalanine (14.7. g, 55.5 mmol), and 1-hydroxybenztriazole hydrate (10.8 g, 70.6 mmol) in DMF (180 ml) was added 1-(3-dimethylamino-propyl-3-ethylcarbodiimide (13.5 g, 70.6 mmol). The mixture was stirred at ambient temperature for 2 h. The reaction was concentrated to remove DMF, diluted with ethyl acetate (1 L), and washed with 5% citric acid (400 mL), water (100 mL), and 10% sodium bicarbonate (200mL). The organic extract was dried over Na₂SO₄, and evaporated to a white foam. Carried on without purification. To a stirred solution of 2-(tert-Butoxycarbonylamino)-N-[2-oxo-5-cyclopropyl-1-(2,2,2-trifluoroethyl)-2,3-dihydro-1H-benzo[e][1,4]diazepin-3-yl]-3-phenyl-propionamide in ethyl acetate (500 mL) at 0° C. was bubbled HCl gas for 1 h. The reaction was evaporated under reduced pressure, the residue taken up in ice cold sat. NaHCO₃ (400 mL) and methylene chloride (500 mL). The phases were separated and the aqueous extracted again with methylene chloride (300 mL). The organic extracts were combined, dried over Na₂SO₄ and evaporated under reduced pressure to give an oil. This was chromatographed over silica eluting with ethyl acetate/methanol/NH₄OH (99/1/0.2). The upper R_f spot was isolated and evaporated under reduced pressure to give a white solid.

¹H NMR (CDCl₃, 300 MHz) δ

Step D. Preparation of (+)-3-Amino-5-cyclopropyl-1-(2,2,2-trifluoroethyl)-1H-benzo[e][1,4]diazepine.

To a stirring solution of 2-amino-N-[2-oxo-5-cyclopropyl-1-(2,2,2-trifluoroethyl)-2,3-dihydro-1H-benzo[e][1,4]diazepin-3-yl]-3-phenyl-propionamide (1.77 g, 3.98 mmol) in methylene chloride (20 ml) was added phenyl isothiocyanate (0.584 mL, 4.80 mmol). The reaction was stirred at ambient temperature for 6 hours, concentrated in vacuo and solid triturated from hexane (50 mL) to give 2.30 g (100%). The solid was added to a stirred −10° C. solution of trifluoroacetic acid (40 mL) under argon, and the mixture stirred at −10° C. until dissolved (15 min.). Upon dissolution the reaction was aged at +4° C. for 20 hours. The reaction was then concentrated in vacuo ≦0° C. and residue flushed with methylene chloride (2×20 mL). The residue was then chromatographed on silica using methylene chloride:methanol: acetic acid:water (90:10:1:1). The lower R_f (0.3) spot was collected and washed with 100 mL satd. NaHCO₃, dried over Na₂SO₄ and evaporated under reduced pressure to give 0.98 g (82%) of a white powder.

¹H NMR (CDCl₃, 300 MHz) δ7.78 (dd, J=8.0 and 1.7 Hz,1H), 7.54 (dt, J=8.0 and 1.7 Hz, 1H), 7.36 (dt, J=8.0 and 1.7 Hz, 1H), 7.30 (br d, J=8.0 Hz,1H), 5.10 (dq, J=25 and 9 Hz,1H), 4.35 (s,1H), 4.15 (approx. sextet, J=8.0 Hz, 1H), 2.22 (br s, 2H), 1.98 (m, 1H), 0.9–1.15 (m, 4H).

Step E: Preparation of:(+)-2-(2,4-Dichlorophenyl)-N-[2,3-dihydro-1-(2,2,2-trifluoroethyl)-2-oxo-5-cyclopropyl-1 H -1,4-benzodiazepin -3-yl]acetamide.

To a stirring solution of (+)-3-amino-5-cyclopropyl-1-(2, 2,2-trifluoroethyl)-1H-benzo[e][1,4]diazepine (0.10 g, 0.337 mmole) in DMF (2 mL) was added 1-hydroxybenztriazole hydrate (72 mg, 0.471 mmol), 2,4-dichlorophenylacetic acid (83 mg, 0.404 mmol), N-methylmorpholine (0.52 u L, 0.471 mmole), and (1-(3-dimethylamino-propyl- 3-ethylcarbodiimide (90 mg, 0.471 mmol). This was stirred at ambient temperature for 2 hours. The reaction was diluted with 10% citric acid (20 mL) and extracted with ethyl acetate (2×40 mL). The combined organics were washed with 10% sodium bicarbonate (20 mL) dried over Na₂SO₄, and evaporated to a white foam. This was chromatographed over silica eluting with 30% ethyl acetate/hexane. The pure fractions were collected and evaporated under reduced pressure to give 141 mg of a white foam which was precipitated from cyclohexane to give 130 mg of a white powder. mp=103°–105° C., [a]D=+17.95° (CHCl3)

¹H NMR (CDCl₃, 300 MHz) δ7.78 (dd, J=7.8 and 1.6 Hz,1H), 7.54 (dt, J=7.8 and 1.6 Hz, 1H), 7.2–7.44 (m, 5H), 7.01(br d, J=7.9 Hz,1H), 5.40 (d, J=10.2 Hz,1H), 5.10 (approx. sextet, J=8.6 Hz, 1H), 4.10 (approx. sextet, J=8.6 Hz, 1H), 3.75 (s, 2H), 1.98 (m, 1H), 0.8–1.1 (m, 4H).

Analysis Calcd. for C₂₂H₁₈Cl₂F₃N₃O₂: C, 54.56; H, 3.75; N, 8.68; Found: C, 54.18; H, 3.78; N, 8.59.

The following examples were prepared in a similar manner as described for Example 1, Step E.

Example 2

(+)-2-(3,4-Dichlorophenyl)-N-[2-oxo-5-cyclopropyl-1-(2,2,2-trifluoroethyl)-2,3-dihydro -1H -benzo [e] [1,4]diazepin-3-yl]-acetamide.

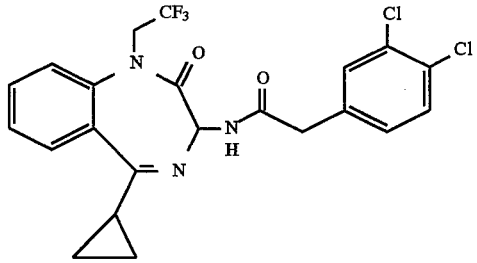

mp=193°–194° C.; [α]D=+18.5° (CHCl3)

¹H NMR (CDCl₃ 300 MHz) δ7.79 (dd, J=7.8 and 1.6 Hz,1H), 7.55 (dt, J=7.8 and 1.6 Hz,1H), 7.4 (m, 2H), 7.30(d, J=8.6Hz, 1H), 7.16 (dd, J=8.6 and 1.6 Hz, 1H), 6.97 (br d, J=7.9 Hz,1H), 5.37 (d, J=8.7 Hz,1H), 5.10 (sextet, J=8.7 Hz, 1H), 4.10 (sextet, J=8.7 Hz, 1H), 3.60 (s, 2H), 1.98 (m, 1H), 0.8–1.1 (m, 4H).

Analysis Calcd. for C₂₂H₁₈Cl₂F₃N₃O₂.0.6 H₂O: C, 53.37; H, 3.91; N, 8.49. Found: C, 53.37; H, 3.77; N, 8.49.

Example 3

(+)-2-(3,5-Dichlorophenyl)-N-[2-oxo-5-cyclopropyl-1-(2,2,2-trifluoroethyl)-2,3-dihydro-1H-benzo[e][1,4]diazepin-3-yl]acetamide

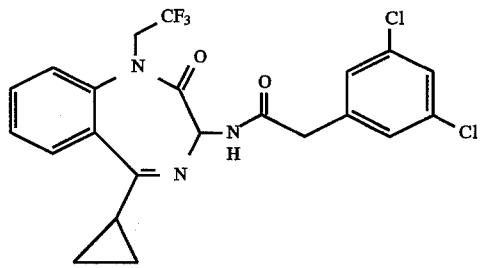

mp=152°–153° C., [α]D=+16.0° (CHCl3)

$^1$H NMR (CDCl$_3$,300 MHz) δ7.79 (dd, J=7.8 and 1.6 Hz, 1H), 7.55 (dt, J=7.8 and 1.6 Hz,1H), 7.2–7.4 (m, 5H), 7.00 (br d, J=8.3 Hz,1H), 5.37 (d, J=8.3 Hz,1H), 5.10 (sextet, J=8.7 Hz, 1H), 4.10 (sextet, J=8.7 Hz, 1H), 3.58 (s, 2H), 2.0 (m, 1H), 0.8–1.1 (m, 4H).

Analysis Calcd. for $C_{22}H_{18}Cl_2F_3N_3O_2 \cdot 0.15$ H20: C, 54.25; H, 3.79; N, 8.63; Found: C, 54.24; H, 3.77; N, 8.36.

Example 4

(+)-3-(2,4-Dichlorophenyl)-N-[2-oxo-5-cyclopropyl-1-(2,2,2-trifluoroethyl)-2,3-dihydro-1H-benzo[e][1,4]diazepin-3-yl]propanamide

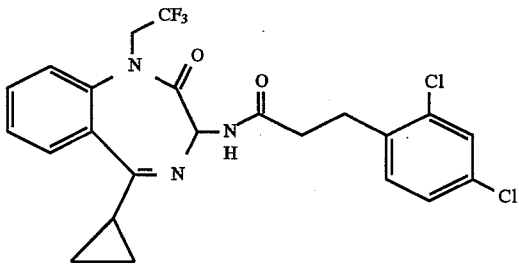

mp=64°–66° C., [α]D=+10.3° (CHCl3)

$^1$H NMR (CDCl$_3$,300 MHz) δ7.80 (d, J=8.1Hz, 1H), 7.55 (t, J=8.1Hz, 1H), 7.1–7.4 (m, 5H), 6.92 (br d, J=8.1 Hz, 1H), 5.40 (d, J=8.8 Hz, 1H), 5.08 (sextet, J=8.7 Hz, 1H), 4.12 (sextet, J=8.7 Hz, 1H), 3.02 (t, 2H), 2.54 (t,2H), 1.98 (m, 1H), 0.8–1.2 (m, 4H).

Analysis Calcd. for $C_{23}H_{20}Cl_2F_3N_3O_2$: C, 55.44; H, 4.05; N, 8.43; Found C, 55.39; H, 4.27; N, 8.21.

Example 5

(+)-2-(4-Trifluoromethylphenyl)-N-[2-oxo-5-cyclopropyl-1-(2,2,2-trifluoroethyl)-2,3-dihydro-1H-benzo[e][1,4]diazepin-3-yl]acetamide.

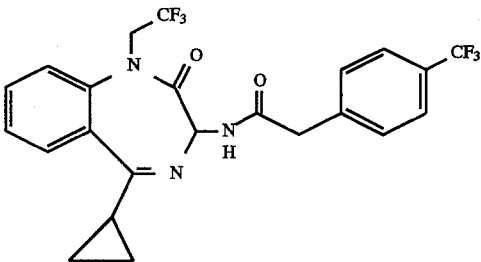

mp=225°–227° C.; [α]D=+41.8° (CHCl3)

$^1$H NMR (CDCl$_3$,300 MHz) δ7.78 (d, J=7.8 Hz,1H), 7.20–7.65 (m, 7H), 6.99 (br d, J=7.9 Hz,1H), 5.39 (d, J=8.2 Hz,1H), 5.08 (sextet, J=8.7 Hz, 1H), 4.10 (sextet, J=8.7 Hz, 1H), 3.69 (s, 2H), 1.98 (m, 1H), 0.8–1.1 (m, 4H).

Analysis Calcd. for $C_{23}H_{19}F_6N_3O_2 \cdot 0.05$ Hexane: C, 57.38; H, 4.07; N, 8.62; Found: C, 57.58; H, 3.99; N, 8.72.

Example 6

(+)2-(3,5-Bis-trifluoromethylphenyl)-N-[2-oxo-5-cyclopropyl-1-(2,2,2-trifluoroethyl)-2,3-dihydro-1H-benzo[e][1,4]diazepin-3-yl]-acetamide.

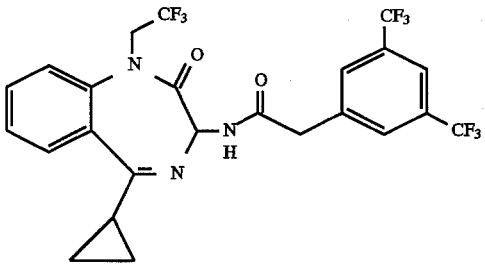

mp=106°–108° C.; [α]D=+32.9° (CHCl3)

$^1$H NMR (CDCl$_3$,300 MHz) δ7.7–7.85 (m, 3H), 7.55 (dt, J=7.8 and 1.6 Hz, 1H),7.38 (t, J=8.6 Hz,1H), 7.31(d, J=8.6Hz, 1H), 7.10 (br d, J=8.0 Hz, 1H), 5.40 (d, J=8.4 Hz, 1H), 5.09 (sextet, J=8.6 Hz, 1H), 4.12 (sextet, J=8.6 Hz, 1H), 3.78 (s, 2H), 1.98 (m, 1H), 0.8–1.1 (m, 4H).

Analysis Calcd. for $C_{24}H_{18}F_9N_3O_2 \cdot 0.10$ Hexane: C, 52.76; H, 3.49; N, 7.50; Found: C, 52.76; H, 3.36; N, 7.73.

Example 7

(+)-2-(2,4-Bis-trifluoromethylphenyl)-N-[2-oxo-5-cyclopropyl-1-(2,2,2-trifluoroethyl)-2,3-dihydro-1H-benzo[e][1,4]diazepin-3-yl]acetamide.

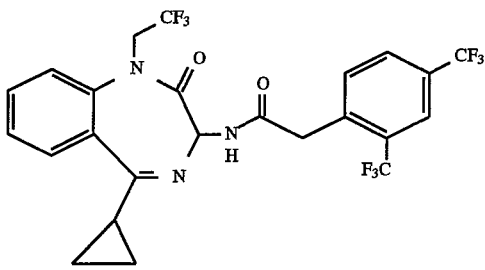

mp=66°–68° C.; [α]D=+33.1° (CHCl3)

$^1$H NMR (CDCl$_3$,300 MHz) δ7.91 (s, 1H), 7.78 (d, J=8.6 Hz, 2H), 7.67 (d, J=8.6 Hz,1H), 7.54(dt, J=8.6 and 1.6 Hz, 1H), 7.37 (t, J=8.6, 1H), 7.29 (d, J=8.6 Hz, 1H), 7.02 (br d, J=8.6 Hz,1H), 5.38 (d, J=8.6 Hz,1H), 5.10 (sextet, J=8.7 Hz, 1H), 4.11 (sextet, J=8.7 Hz,1H), 3.60 (s, 2H), 1.98 (m, 1H), 0.8–1.1 (m, 4H).

Analysis Calcd. for C$_{24}$H$_{18}$F$_9$N$_3$O$_2$.0.10 Hexane: C, 52.76; H, 3.49; N, 7.50; Found: C, 52.93; H, 3.42; N, 7.66.

What is claimed is:

1. The compounds of formula I

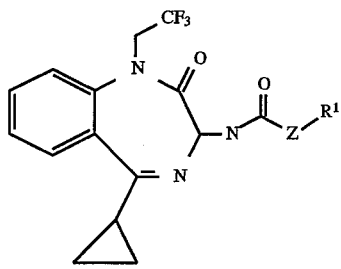

FORMULA I where

Z is C$_{0-6}$ alkyl; and

R$^1$ is phenyl or mono or disubstituted phenyl, where the substitutents are Cl, and CF$_3$, or pharmaceutically acceptable salts, hydrates and crystal forms thereof.

2. A pharmaceutical formulation comprising a pharmaceutically acceptable carrier and a therapeutically effective amount of the compound of claim 1 or a pharmaceutically acceptable salt, crystal form or hydrate thereof.

3. The pharmaceutical formulation of claim 2 comprising in addition another antiarrhythmic agent or other cardiovascular agent.

4. A method of preventing or treating arrhythmia which comprises the administration to a patient in need of such treatment of an antiarrhythmically effective amount of the compound of claim 1.

5. The method of claim 4 comprising the concomitant administration of another antiarrhythmic agent or other cardiovascular agent.

6. The compounds of claim 1 selected from (+)-2-(2,4-Dichlorophenyl)-N-[2,3-dihydro-1-(2,2,2-trifluoroethyl)-2-oxo-5-cyclopropyl-1H-1,4-benzodiazepin-3-yl]acetamide

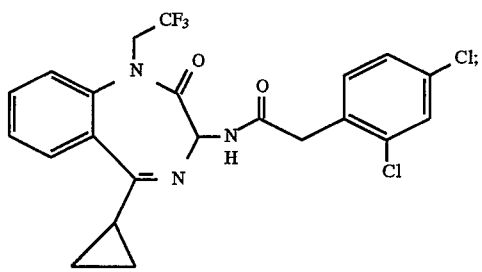

(+)-2-(3,4-Dichlorophenyl)-N-[2-oxo-5-cyclopropyl-1-(2,2,2-trifluoroethyl)-2,3-dihydro-1H-benzo[e][1,4]diazepin-3-yl]-acetamide

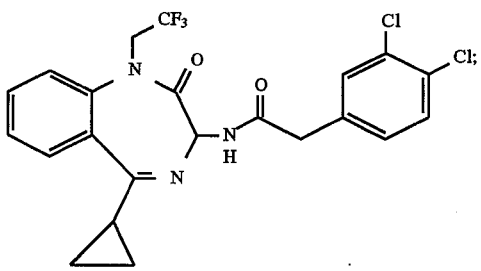

(+)2-(3,5-Dichlorophenyl)-N-[2-oxo-5-cyclopropyl-1-(2,2,2-trifluoroethyl)-2,3-dihydro-1H-benzo[e][1,4]diazepin-3-yl]acetamide

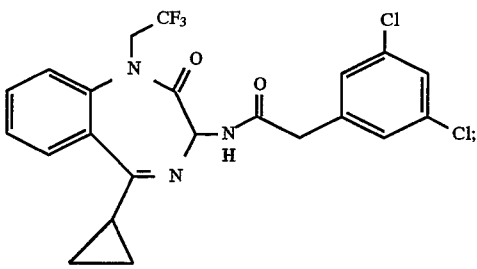

(+)-3-(2,4-Dichlorophenyl)-N-[2-oxo-5-cyclopropyl-1-(2,2,2-trifluoroethyl)-2,3-dihydro-1H-benzo[e][1,4]diazepin-3-yl]propanamide

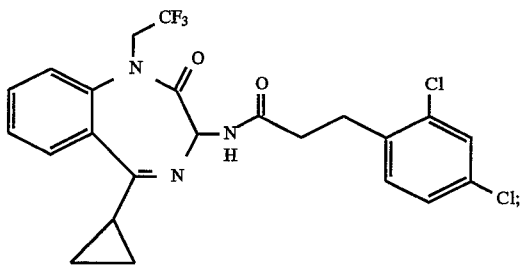

(+)-2-(4-Trifluoromethylphenyl)-N-[2-oxo-5-cyclopropyl-1-(2,2,2-trifluoroethyl)-2,3-dihydro-1H-benzo[e][1,4]diazepin-3-yl]acetamide

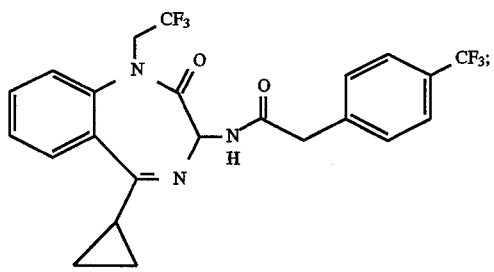

(+)-2-(3,5-Bis-trifluoromethylphenyl)-N-[2-oxo-5-cyclopropyl-1-(2,2,2-trifluoroethyl)-2,3-dihydro-1H-benzo[e][1,4]diazepin-3-yl]-acetamide

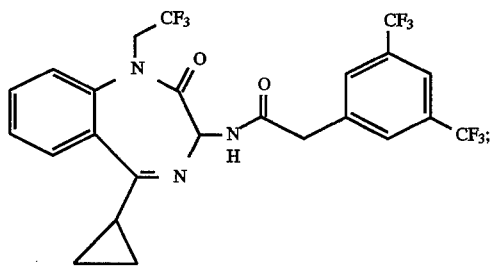

and (+)2-(2,4-Bis-trifluoromethylphenyl)-N-[2-oxo-5-cyclopropyl-1-(2,2,2-trifluoroethyl)-2,3-dihydro-1H-benzo[e][1,4]diazepin-3-yl]acetamide

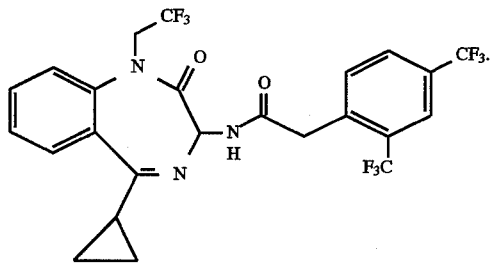

7. The compound of claim 1 which is (+)-2-(2,4-Dichlorophenyl)-N-[2,3-dihydro-1-(2,2,2-trifluoroethyl)-2-oxo-5-cyclopropyl-1H-1,4-benzodiazepin-3-yl]acetamide

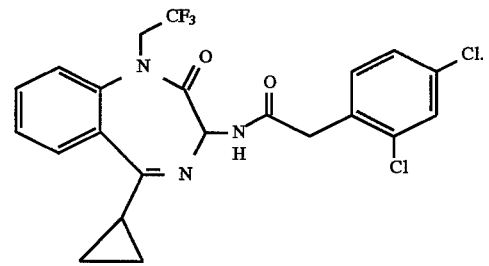

8. The compound of claim 1 which is (+)-2-(3,4-Dichlorophenyl)-N-[2-oxo-5-cyclopropyl-1-(2,2,2-trifluoroethyl)-2,3-dihydro-1H-benzo[e][1,4]diazepin-3-yl]-acetamide

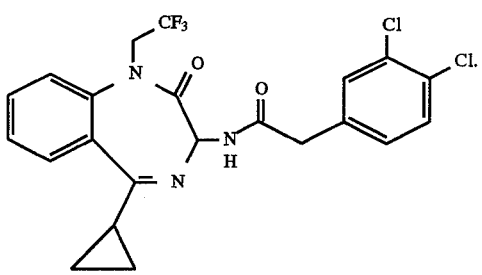

9. The compound of claim 1 which is (+)-2-(3,5-Dichlorophenyl)-N-[2-oxo-5-cyclopropyl-1-(2,2,2-trifluoroethyl)-2,3-dihydro-1H-benzo[e][1,4]diazepin-3-yl] acetamide

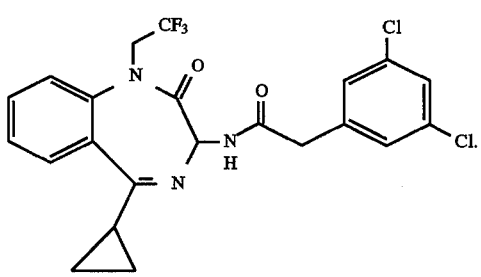

10. The compound of claim 1 which is (+)-3-(2,4-Dichlorophenyl)-N-[2-oxo-5-cyclopropyl-1-(2,2,2-trifluoroethyl)-2,3-dihydro -1H-benzo[e][1,4]diazepin-3-yl] propanamide

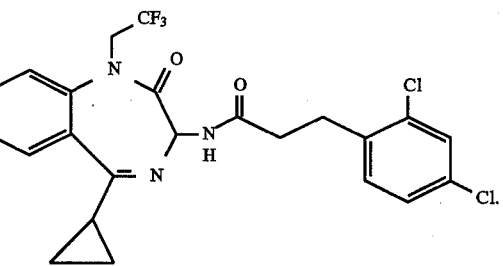

11. The compound of claim 1 which is (+)-2-(4-Trifluoromethylphenyl)-N-[2-oxo-5-cyclopropyl-1-(2,2,2-trifluoroethyl)-2,3-dihydro-1H-benzo [e][1,4]diazepin-3-yl] acetamide

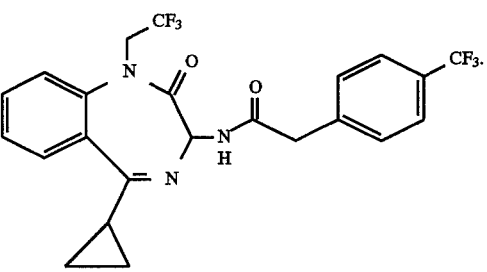

12. The compound of claim 1 which is (+)-2-(3,5-Bis-trifluoromethylphenyl)-N-[2-oxo-5-cyclopropyl-1-(2,2,2-trifluoroethyl)-2,3-dihydro-1H-benzo[e][1,4]diazepin-3-yl]-acetamide

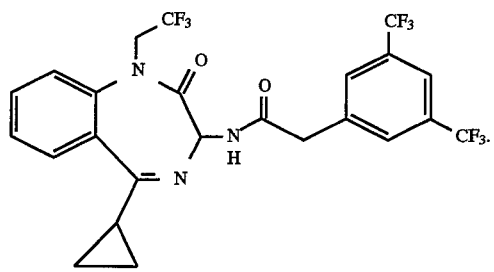
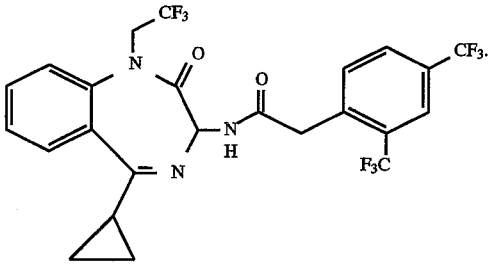
trifluoroethyl)-2,3-dihydro-1H-benzo[e][1,4]diazepin-3-yl]
acetamide
13. The compound of claim 1 which is (+)-2-(2,4-Bis-
trifluoromethylphenyl)-N-[2-oxo-5-cyclopropyl-1-(2,2,2-
\* \* \* \* \*